US009364524B2

(12) United States Patent
Junco Barranco et al.

(10) Patent No.: US 9,364,524 B2
(45) Date of Patent: Jun. 14, 2016

(54) PHARMACEUTICAL COMPOSITION USING GONADOTROPIN-RELEASING HORMONE (GNRH) COMBINED VARIANTS AS IMMUNOGEN

(71) Applicant: Centro de Ingenieria Genetica Y Biotecnologia, Ciudad de la Habana (CU)

(72) Inventors: Jesus Arturo Junco Barranco, Camaguey (CU); Osvaldo Reyes Acosta, Ciudad de la Habana (CU); Eddy Emilio Bover Fuentes, Camaguey (CU); Franklin Fuentes Aguilar, Camaguey (CU); Eulogio Pimentel Vazquez, Camaguey (CU); Roberto Basulto Baker, Camaguey (CU); Gerardo Enrique Guillen Nieto, Ciudad Habana (CU); Yovisleidys Lopez Saez, Camaguey (CU); Hilda Elisa Garay Perez, Ciudad Habana (CU); Lesvia Calzada Aguilera, Camaguey (CU); Maria Castro Santana, Camaguey (CU); Niurka Oneysi Arteaga More, Camaguey (CU); Luis Alberto Aguero Barrocal, Camaguey (CU)

(73) Assignee: CENTRO DE INGENIERIA GENETICA Y BIOTECNOLOGIA, Ciudad de la Habana (CU)

( * ) Notice: Subject to any disclaimer, the term of this patent is extended or adjusted under 35 U.S.C. 154(b) by 0 days.

(21) Appl. No.: 14/662,482

(22) Filed: Mar. 19, 2015

(65) Prior Publication Data

US 2015/0190491 A1 Jul. 9, 2015

Related U.S. Application Data

(62) Division of application No. 13/121,915, filed as application No. PCT/CU2009/000007 on Sep. 30, 2009, now Pat. No. 8,999,931.

(30) Foreign Application Priority Data

Sep. 30, 2008 (CU) .................................... 2008-0185

(51) Int. Cl.
*A61K 39/00* (2006.01)
*A61K 38/09* (2006.01)
*A61K 47/48* (2006.01)

(52) U.S. Cl.
CPC ............. *A61K 39/0011* (2013.01); *A61K 38/09* (2013.01); *A61K 39/0006* (2013.01); *A61K 47/4833* (2013.01); *A61K 47/48261* (2013.01); *A61K 2039/585* (2013.01); *A61K 2039/6037* (2013.01)

(58) Field of Classification Search
None
See application file for complete search history.

(56) References Cited

U.S. PATENT DOCUMENTS

| 4,608,251 | A | 8/1986 | Mia |
| 5,897,863 | A | 4/1999 | Robson et al. |
| 6,132,720 | A | 10/2000 | Grimes et al. |
| 6,783,761 | B2 | 8/2004 | Grimes et al. |
| 2002/0076416 | A1 | 6/2002 | Grimes et al. |
| 2005/0095258 | A1 | 5/2005 | Campos et al. |

FOREIGN PATENT DOCUMENTS

| WO | 90/11298 | 10/1990 |
| WO | 98/27111 A1 | 6/1998 |

OTHER PUBLICATIONS

Valerie A. Ferro, et al., "Influence of Carrier Protein Conjugation Site and Terminal Modification of GnRH-I Peptide Sequence in the Development of a Highly Specific Anti-fertility Vaccine. Part I", American Journal of Reproductive Immunology, ISSN 8755-8920, vol. 48, No. 6, p. 361-371, © Blackwell Munksgaard, 2002.

G.P. Talwar, et al., "Immunotherapy and fertility control by immunization against gonadotrophin-releasing hormone", Section: "Sites for carrier conjugation and their implications", National Institute of Immunology, New Delhi, India, Current Opinion in Immunology 1990, vol. 2: No. 5, p. 733-735, © Current Biology Ltd ISSN 0952-7915.

(Continued)

*Primary Examiner* — Christina Borgeest
(74) *Attorney, Agent, or Firm* — Hoffmann & Baron, LLP

(57) ABSTRACT

A pharmaceutical composition using natural gonadotropin—releasing hormone (GnRH), and/or some of its mimetic peptides, indistinctly bound by its amino or carboxyl extremes to a carrier molecule; in one case by its carboxyl extreme and in the other case by the amino terminal extreme, thus eliciting a faster and more potent immunological response against the endogenous GnRH hormone. This finally leads to the ablation of the GnRH and consequently of the rest of the involved hormones in the stream GnRH/LH-FSH/Testosterone-(estrogens). An advantage of this formulation consists on facilitating the exposition to the immune system of a greater number of epitopes of the GnRH or its mimetics, minimizing thus the steric hindrance produced by the carriers. This invention has a direct application in the castration of pets and animals of economic interest, in the control of human fertility as well as in the treatment of hormone-sensitive tumors, such as that of the prostate, the breast, ovary, the endometry, testicles, hypophysis, salivary glands and other kinds of human tumors.

4 Claims, 6 Drawing Sheets

(56) References Cited

OTHER PUBLICATIONS

Figures 1, 2:
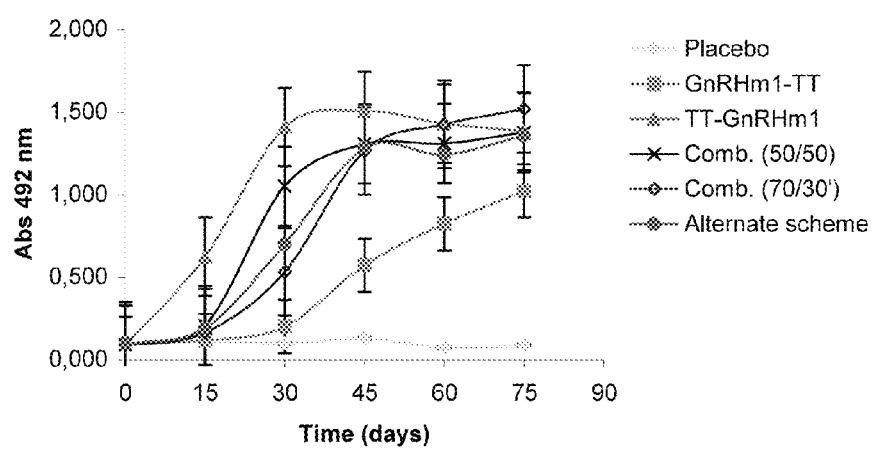

D.W. Silversides, et. al., "A synthetic luteinizing hormone releasing hormone vaccine—I. Conjugation and specificity trials in BALB/c mice", Journal of Reproductive Immunology, vol. 13, No. 3 (1988), p. 249-261, © 1988 Elsevier Scientific Publishers Ireland Ltd.

Valerie A. Ferro, et. al., "Immunoneutralisation of GnRH-I, without cross-reactivity to GnRH-II, in the development of a highly specific anti-fertility vaccine for clinical and veterinary use", Journal of Reproductive Immunology, vol. 51, No. 2, (2001), p. 109-129, © 2001 Elsevier Science Ireland Ltd.

Charles Huggins, et al., "Studies on Prostatic Cancer. I. The Effect of Castration, of Estrogen and of Androgen Injection on Serum Phosphatases in Metastatic Carcinoma of the Prostate", Cancer Research 1941; 1: p. 293-297, © 1941 American Associate for Cancer Research.

Andrew V. Schally, et al., "Antitumor Effects of Analogs of Hypothalamic Hormones in Endocrine-Dependent Cancers", Proceedings of the Society for Experimental Biology and Medicine, 175, p. 259-281 (1984), © 1984 by the Society for Experimental Biology and Medicine.

R.H. Meloen, et al., "Effcient immunocastration of male pigles by immunoneutraliztion of GnRH using a new GnRH-like peptide", Vaccine, 1994, vol. 12, No. 8, p. 741-746, © 1994 Butterworth-Heinemann Ltd.

William F. Crowley, Jr, et al. , "LHRH Peptides as Female and Male Contraceptives", 29, LHRH in Hypogonadotropic Hypogonadism, Harper & Row, Publishers, Philadelphia, 1981, p. 321-333, © 1981 by Northwestern University.

J.H. Waxman, et al., "Treatment with gonadotrophin releasing hormone analogue in advanced prostatic cancer", British Medical Journal, vol. 286, Apr. 23, 1983, p. 1309-1312.

J.M. Allen, et al. "Advanced carcinoma of the prostate: treatment with a gonadotropin releasing hormone agonist", British Medical Journal, vol. 286, May 21, 1983, p. 1607-1609.

Steeve Couillard, et al., "Effect of Dehydroepiandrosterone and the Antiestrogen EM-800 on Growth of Human ZR-75-1 Breast Cancer Xenografts", Journal of the National Cancer Institute, vol. 90, No. 10, May 20, 1998, p. 772-778.

Sabine Kolle, et al., "Expression of growth hormone receptor in human prostatic carcinoma and hyperplasia", International Journal of Oncology, vol. 14, No. 5, p. 911-916, 1999.

Carlos Gual, M.D., et al., "Ability of an anti-luteinizing hormone-releasing hormone vaccine to inhibit gonadotropins in postmenopausal women", Fertility and Sterility, vol. 67, No. 2, Feb. 1997, p. 404-407, © 1997 American Society for Reproductive Medicine.

G.P. Talwar, et al., "A recombinant luteinising-hormone-releasing-hormone immunogen bioeffective in causing prostatic atrophy", Vaccine 22 (2004) p. 3713-3721, © 2004 Published by Elsevier Ltd.

R.P. Millar, et al., "Gonadotrophin-releasing hormone—diversity of functions and clinical applications", South African Medical Journal 1987, vol. 72, 5 DES 1987, p. 748-755.

R.M. Hoskinson, et al., "Vaxstrate®: An Anti-reproductive Vaccine for Cattle", Australian Journal of Biotechnology, vol. 4, No. 3, Jul. 1990, p. 166-170.

M. Bonneau, et al., "The effects of immunization against luteinizing hormone-releasing hormone on performance, sexual development, and levels of boar taint-related compounds in intact male pigs", Journal of Animal Science 1994, 72, p. 14-20.

Alain Caraty, et al. "The effect of active immunisation against LHRH on LH and FSH secretion and on fat androstenone level in entire male pigs", C.R. Acad. Sc. Paris, t. 303, Serie III, No. 16, 1986, p. 673-676.

R.E. Falvo, et al., "Effect of Active Immunization against LHRH or LH in Boars: Reproductive Consequences and performance Traits", Journal of Animal Science, 1986, 63, p. 986-994.

G.P. Talwar, "Vaccines for control of fertility and hormone-dependent cancers", Immunology and Cell Biology (1997), 75, p. 184-189.

Marie-Paule Schutze, et al, "Carrier-Induced Epitopic Suppression, A Major Issue for Future Synthetic Vaccines", The Journal Immunology, vol. 135, No. 4, Oct. 1985, p. 2319-2322, © 1985 by the American Association of Immunologists.

Amitabh Gaur, et al, "Bypass by an alternate 'carrier' of acquired unresponsiveness to hCG upon repeated immunization with tetanus-conjugated vaccine", International Immunology, vol. 2, No. 2, p. 151-155, © 1990 Oxford University Press 0953-8178/90.

S. Sad, et al., "Carrier-induced suppression of the antibody response to a 'self' hapten", Immunology 1991, 74, p. 223-227.

Connie L. Finstad, et al., "Synthetic luteinizing hormone releasing hormone (LHRH) vaccine for effective androgen deprivation and its application to prostate cancer immunotherapy", Vaccine, 22 (2004), p. 1300-1313, © 2003 Elsevier Ltd.

Testo-CT2, "Testo-CT2 is a radioimmunoassay kit for the quantitative determination of Testosterone in human serum and plasma", Sep. 2004—Model 13 (CISBio, International, France).

SAS Institute, Inc., "SAS/STAT User's Guide", Release 6.03 Editon Cary, NC: 1988, 1028 pp., (SAS®), © 1988 by SAS Institute Inc.

Junco et al., Vaccine, 2007; 25: 8460-8466.

Fuentes et al., Journal of Experimental Therapeutics and Oncology, 2007; 6: 279-284.

Tannock et al., The Basic Science of Oncology—Third Edition; (1987) New York: McGraw-Hill; p. 357.

Limonta et al., Cancer Treatment Reviews, 2013; 39: 647-663.

Bruchovsky et al., Cancer Research, 1990; 50: 2275-2282.

Song et al., Expert Opin Biol Ther., 2007, 7: 431-438.

Natural GnRH  QHWSYGLRPG  (SEQ ID NO. 8)

GnRHm1 – TT  QHWSYPLRPG  GG  QYIKANSKFIGITEL  (SEQ ID NO. 4)

TT - GnRHm1  QYIKANSKFIGITEL  GG  QHWSYPLRPG  (SEQ ID NO. 6 )

PHARMACEUTICAL COMPOSITION USING GONADOTROPIN-RELEASING HORMONE (GNRH) COMBINED VARIANTS AS IMMUNOGEN

CROSS-REFERENCE TO RELATED APPLICATIONS

This application is a divisional application of U.S. application Ser. No. 13/121,915, filed on Mar. 30, 2011, which is a U.S. National Phase of International Application No. PCT/CU2009/000007, filed Sep. 30, 2009, which claims priority from Cuban Application No. CU 2008-0185, filed Sep. 30, 2008, all of which are incorporated herein by reference.

TECHNICAL SCOPE

The present invention deals with the field of immunology, endocrinology, oncology, reproduction, and it is particularly based on the simultaneous generation of a potent immune response against all of the GnRH molecule; mainly against the carboxyl and amino extremes of the hormone, thus taking advantage of the best exposition to the immune system of the GnRH molecule, either in its native or in its mimetic form including variants based on the D amino-acids, when these are bound to a carrier molecule; in one case by the carboxyl extreme and in the other by the amino terminal so as to form 2 different immune-molecules. This will be further referred to as carboxyl terminal variant and amino terminal variant respectively.

PRIOR STATE OF THE ART

The gonadotropin-releasing hormone (GnRH), also known as Luteinizing hormone-releasing hormone (LHRH), is a hypothalamic decapeptide that acts upon the anterior hypophysis causing the release of the follicle-stimulating hormone (FSH) and the Luteinizing hormone (LH) towards the blood. This at the same time stimulates the testicular steroids synthesis along with the development of male gonads in young and in adolescent males as well. As to the female sex, this hormone stimulates the development of ovaries, follicles, and the synthesis of the ovary steroids as well as ovulation.

The role of the LHRH in the regulation of fertility is well known. Thus, a great number of diseases are related to the gonodatropines and the gonodal steroid hormones, particularly the estrogens and the testosterone. Such diseases include the breast cancer, uterus and other kinds of gynecological cancer, or diseases, such as endometry, uterine fibrosis, prostate cancer, and benign prostatic hyperplasia.

Castration, also known as gonadectomy, either surgical or chemical, constitutes one of the most effective methods in the therapeutic intervention of hormone-dependent neoplasia (Huggins C, Hodges C V. Studies on prostatic cancer. I. The effect of castration, of estrogen and of androgen injection on serum phosphatases in metastatic carcinoma of the prostate. Cancer Research 1941; 1: 293-7). In the branch of livestock production, castration is practiced to avoid the unpleasant smell and taste of meat from adult male animals that are of economic importance. (Proc. Soc. Exp. Biol. Med 175:259-281, 1984. Meloen R H et al. Efficient immunocastration of male piglets by immunoneutralization of GnRH using a new GnRH-like peptide. Vaccine 1994; 12: 741-747. Crowley W F, Vale W W, Rivier J, MacArthur J W: LHRH in hypogonadotropic hypogonadism. In Zatuchni G L, Shelton J D, Sciarra J J (eds): "LHRH Peptides as Female and Male Contraceptives". Philadelphia: Harper and Row Publishers, 1981, pp 321-333).

Analogues of GnRH are among the most used drugs for treating prostate, ovary and breast cancer. They exert their action through the estrogenic or androgenic deprivation and/or the direct effect over the cancer cells. (Schally, Comaru-Schally A M, Redding T W: Anti-tumor effects of analogues of hypothalamic hormones in endocrine-dependent cancers). The direct mechanism through which these GnRH analogues and antagonists exert their action has been linked to the desensitization and deregulation of the GnRH receptors when they are administered chronically. Several of these potent analogues and antagonists have been reported by different authors (Waxman J H, Wass J A H, Hendry W F, Whitfield H N, Besser G M, Malpas J S, Oliver R T D: Treatment with gonadotropin releasing hormone analogue in advanced prostate cancer. Br. Med. J. 286:1309-1312, 1983. Allen J M, O'Shea J P, Mashiter K, Williams G, Bloom S R: Advanced carcinoma of the prostate: Treatment with a gonadotropin releasing hormone agonist. Br. Med. J. 286:1607-1609, 1983). (Couillard S. Labrie C. Belanger A. Candas B. Pouliot F. Labrie F. "Effect of dehydroepiandrosterone and the antiandrogen EM-800 on growth of human ZR-75-1 breast cancer xenografts". J. Nat. Cancer Inst., May 20, 772-778, 1998; Kolle S. et al.: "Expression of growth hormone receptor in human prostatic carcinoma and hyperplasia". Int. J. Oncol., vol. 14, No. 5, p 911-916, 1999).

An alternative variant when using analogues of GnRH/LHRH is the active immunization with the native hormone or with its mimetic peptides, which can serve as vaccines when they are bounds to more immunogenic molecules such as the tetanus toxoid, diphtheria toxoid or its epitopes, KLH (Keyhole Limpet Hemocyanin) or BSA (bovine serum albumin), among others (Gual C, Garza-Flores J, Menjivar M, Gutierrez-Najar A, Pal R, Talwar G P. Ability of an anti-Luteinizing hormone-releasing hormone vaccine to inhibit gonadotropins in postmenopausal women. Fertil Steril 1997; 67: 404-7).

Different reports have been published about vaccination using GnRH/LHRH as a proper antigen, e.g. U.S. Pat. No. 5,897,863; U.S. Pat. No. 6,132,720. However, one of the existing problems since the beginning of this practice is the insufficient capacity in eliciting a potent immune response to produce effective levels of anti-GnRH antibodies. This is mainly due to the small size and the autologous nature of this decapeptide in all mammals. That is why, since the first attempts, the experience accumulated with similar molecules and the use of carriers that increase the visibility of this peptides for the immune system have been of great help.

Experiments with vaccine candidates based on the GnRH or its mimetic peptides bound to carrier molecules of tetanus toxoid have been trialed in male pigs, rodents and primates. These experiments showed atrophy of testicles, prostate as well as ovary in females (Talwar G P, Raina K, Gupta J. C, Ray R, Wadhwa S, Ali M M. A recombinant Luteinizing-hormone-releasing hormone immunogen bioeffective in causing prostatic atrophy. Vaccine 2004; 22:3713-372. Millar R P, King J A, Davidson J S, Milton R C. Gonadotropin-releasing hormone-diversity of functions and clinical applications. S Afr Med J 1987; 72: 748-755). The great variability of the results observed among the individuals of an immunized group, even when large doses are used, is another disadvantage frequently referred to when using GnRH/LHRH based immunogens as vaccines against fertility in pets and animals of economic interest. This is compounded by the problematic use of highly reactogenic adjuvants, such as the Freund complete adjuvant (Hoskinson et al, Austr. J. Biotech;

4, 166-170 (1990); Bonneau et al., J. Anim. Sci. 72, 14-20 (1994); U.S. Pat. No. 4,608,251; Int. patent appl. WO 88205109; Caraty et al., C. R. Acad. Sc. Paris, t. 303, Serie III, No. 16, 673-676 (1986); Falvo et al.; J. Anim. Sci. 63, 986-994 (1986).

Similarly the WO 98/27111 patent "Preparado vacunal para la inmunocastracion reversible de mamfferos" by R. Bringas et al., describes positive results regarding immunocastration of prepuberous pigs using mutated GnRH bound to tetanus toxoid (TT) in the synthesis process and adjuvated in complete Freund's adjuvant (CFA). However, the extensive use of this vaccine preparation did not show the observed homogeneity in puberous animals.

The first clinical trials in patients with advanced prostate cancer, as well as in post-menopausal women, in order to research about the gonadotropin inhibition, where carried out for the first time in the decade of 90 of the past century, which where published by Talwar G P, et al ((Talwar G P. Vaccines for control of fertility and hormone-dependent cancers. Immunology and Cell Biology 1997; 75: 184-189. Gual C, Garza-Flores J, Menjivar M, Gutierrez-Najar A, Pal R, Talwar G P. Ability of an anti-Luteinizing hormone-releasing hormone vaccine to inhibit gonadotropins in post-menopausal women. Fertil Steril 1997; 67: 404-7). Beside the above mentioned the candidates that have been used LHRH chemically conjugated to tetanus toxoid (TT) and to diphtheria toxoid (DT) as carriers, frequently produce anti-haptenic immune-suppression (Schutze M-P, Leclerc C, Jolivet M, Audibert F, Chedid L. Carrier-induced epitopic suppression, a major issue for future synthetic vaccines. J immunol 1985; 135: 2319-22. Gaur A, Arunan K, Singh O M, Talwar G P. By pass by an alternate carrier of acquired unresponsiveness to HCG upon repeated immunization with tetanus conjugated vaccine. Int Immunology 1990; 2(2):151-5. Sad S, Gupta H M, Talwar G P, Raghupathy R. Carrier induced suppression of the antibody response to self hapten. Immunlogy 1991; 74:223-7), in addition to the loses reported in the conjugation process (Gual C, Garza-Flores J, Menjivar M, Gutierrez-Najar A, Pal R, Talwar G P. Ability of an anti-Luteinizing hormone-releasing hormone vaccine to inhibit gonadotropins in postmenopausal women. Fertil Steril 1997; 67: 404-7).

Recently, it has been reported that a group of North American researchers have used T. epitopes cooperators originating from micro-organism antigens responsible for frequent infectious infant diseases. These have been bound to GnRH by its amino terminal extreme in the very process of chemical synthesis in order to find a much more potent and universal response (Finstad C. L, Wang C. Y, Kowalsky J, Zhang M, Li M, Li X, Xia W, Bosland M, Murthy k. k, Walfield A, Koff W. C, Zamb T. J. Synthetic Luteinizing hormone releasing hormone (LHRH) vaccine for effective androgen deprivation and its application to prostate cancer immunotherapy. Vaccine 2004; 22: 1300-1313). Nevertheless, despite the good immunological response due to the use of 4 T helper epitopes in the same immunogen, the use of repeated immunization with oily adjuvants was necessary. The said formulation is a difficult process to be reproduced, highly expensive and not easy to be implemented in a major industrial process. In this case, the potentiality of the immunological response is particularly exploited based on the diversity of the carrier molecules, disregarding the potentiality that would offer a mixture where the amino and the carboxyl-free from GnRH or its mimetics-would be present.

Finally, it must be pointed out that there is some literature reporting the immunogenic capacity of different immune-conjugates of GnRH, or their mimetics, as well as the varying results obtained by different authors that have used immune-molecules of GnRH conjugated by their carboxyl and amino extremes, including the use of additional amino-acids that facilitate the conjugation. Likewise, reports are found about the use of different carriers molecules bound to one of its extremes, obtained by conventional synthesis of peptides or by the recombination of DNA, or by complex molecules in the form of "Tandem" and MABS. However, as to the use of a 2 variant formulation of GnRH coupled to a carrier molecule (one through the amino terminal and the other by the carboxyl terminal being used in the same pharmaceutical preparation) no report dealing with the synergic effect upon the immune response, as well as the levels of sexual hormones and the effect on the target organs (prostate, testicles, breast, ovaries) has been found yet. The construction process of the proposed molecules include the chemical binding by synthesis, the conjugation or cloning of the fusion protein of GnRH, or its mimetics with carrier molecules. The carrier molecules may be either complete proteins or their fragments or epitopes, for example: tetanus toxoid, *Nisseria Meningitidis* P64K protein, hepatitis B surface antigen, hepatitis virus core antigen, etc.

The herein pharmaceutical preparation administered in the same formulation generates a synergic immunological response that is targeted against the amino and carboxyl extremes free from GnRH. As a result, a fast and significant ablation of the male and female sexual hormones is obtained (androgens and estrogens respectively), which in terms produces a vigorous immunocastration. This formulation would have a direct application upon the immunocastration of pets and animals of economical interest, as well as in the control of human fertility and in treating hormone-sensitive tumors, such as the prostate, breath, ovary, testicular and endometrial cancers, and also the pituitary and salivary glands and other tumors. The target organs volume reduction, decrease of the tumor mass and an increase of the individuals' survive are among the conspicuous effect of this formulation.

Novelty and Advantages of the Proposed Invention.

The present invention is based on the combination, in the same immunization scheme, of 2 variants of GnRH/LHRH hormone, either natural or by its mimetics, including the retro-inverses variants, synthesized by D amino-acids. Here GnRH variants are generated through chemical synthesis, conjugation or the use of GnRH DNA chimeras bound indistinctly by the amino and carboxyl terminal extremes to a carrier molecule of the TT type, or its epitopes. The obvious aim is to find a faster and more potent immunological response against the endogenous GnRH. In this case, the carboxyl and amino terminal variants (regarding the binding site of GnRH to the carrier molecule) may be administered at the same time in the same preparation, or separated, in a sequential or alternating form in the same immunization scheme.

The novelty of this invention lies on the synergic effect it produces upon the immune system, the active immunization with the 2 GnRH variants mentioned before, referred to as carboxyl terminal (variant in which the carrier is bound to the carboxyl terminal of GnRH or its mimetics) and the amino terminal (variant in which the carrier is bound to the amino terminal of GnRH or its mimetics). Once these variants are administered as part of the same formulation, they produce a fast and potent ablation of the male and female sexual hormones (androgens and estrogens respectively) producing a vigorous immunocastration action. Hence its effectiveness in the immune-castration of pets and animals of economic interest. On the other hand, it can also be used in the control of human fertility, as well as in the treatment of human hormone-sensitive tumors; prostate, breast, ovary, endometrial, testicles, hypophysis, salivary glands, and other tumors. The effect of the treatment is expressed as the target organs volume reduction, decrease of the tumor mass and an increase of the individuals' survival.

The described combination not only represents the sum of actions of the two variants (carboxyl and amino terminal), but also a synergistic effect on the immunological system is similarly expressed on the target organs, once they are administered in the before described combinations.

As an advantage over the previously described treatments, the present invention shows a faster and more potent action on target organs (testicles, prostate, ovary, etc); and/or over the sexual hormone-dependent tumor (prostate, breast, ovary, endometrial, salivary glands, testicles, etc); due to the achieved synergism obtained with the mixture of carboxyl and amino terminal variants.

The combination of the proposed variants shows a close relationship between the obtained titers of anti-GnRH antibodies and the reduction of sexual hormones (androgens and estrogens) to castration levels. This in turn is related to the effect produced over the target organs. These results, besides the effects achieved with the use of oily adjuvants (Montanide) permits the use of other less reactogenic (innocuous) adjuvants; such as aluminum salts. The above mentioned aspects offer a considerable advantage of the mixture of GnRH amino and carboxyl terminal variants over any other GnRH hormone-based immunogen so far reported.

DETAILED DESCRIPTION OF THE INVENTION

The immune response generated by the immunization of healthy adult rats using the GnRH carboxyl and amino terminal peptide variants in the same formulation or vaccine candidate has permitted to obtain better results as compared to other immunization schemes where only an independent variant is used (carboxyl or amino terminal). The described results show synergism both in eliciting immune-castration as in the treatment of benign proliferative diseases (e.g. Endometriosis), or malignant (prostate, breast, endometrial, ovary, testicles, sub-maxillary glands cancers) and others sensitive to a hormonal depletion.

Unlike previously applied techniques, native GnRH molecules or its mimetics, especially GnRHm1, can be directly bound to a carrier protein in the process of peptide synthesis, or chemically conjugated, or cloned in fusion proteins form to highly immunogenic molecules, to form two different variants; carboxyl and amino terminals. These variants can be bound to some of the most frequently reported carrier proteins, or its epitopes, that is tetanus toxoid, diphtheria toxoid P64K protein of *Neisseria meningitides*, hepatitis B surface antigen, hepatitis B core antigen, etc., to achieve a quick and potent immunological response with a synergistic effect leading to GnRH ablation as well as ablation of the hormones involved in the GnRH/LH-FSH/Testosterone/estrogens cascade.

The carboxyl and amino terminal variants can be used in the same formulation as different proportions, where the relation between carboxyl terminal variant and amino terminal can vary from 10:90 to 80:20 (weight/weight) In this way, GnRH molecule that is bound by its carboxyl terminal extreme represent in all cases less than 10% of the total mixture quality, and at the same time the amino terminal variant represents at least a 20% of the total mixture.

The best results with the carboxyl and amino terminal combination are obtained when they are mixed in a 50% (weight/weight) proportion of each variant.

Similarly, GnRH molecules, carboxyl and amino terminals, can be bound indistinctly in the same carrier, in one case by the amino extreme and in the other by the carboxyl extreme. Otherwise, one variant (carboxyl terminal) can be bound to a carrier protein, while the other variant (amino terminal) is bound to another carrier protein. Thus, the immunogenic mixture may be constituted, for example, by GnRH or its mimetics bound in a case to a carrier as TT or one of its epitopes and in the other case to a P64K protein of *Neisseria meningitides*, or the hepatitis B core antigen or its epitopes, or another highly immunogenic carrier molecule.

This kind of combination allows a faster and more potent anti-GnRH immunological response, using mixed GnRH carboxyl and amino terminal variants adjuvated in oily emulsions of the Montanide type, or Hydro soluble adjuvants of the albumin type, and QS 21 as compared to other immunogens.

The potentiality of the described formulation can be ostensibly enhanced with the addition of immune-stimulators such as very small size proteoliposomes (VSSP), obtained from the mixture of *Neisseria meningitides* wall lipoproteins with N-Acetyl or N-glycolyl GM3 gangliosides or similarly when it is mixed with hydro soluble adjuvants like cocleates and arginates.

As it has been mentioned before, this invention can be used for the immunization of a wide range of vertebrates and its use in the mammal fertility control in pets (dogs, cats, etc), in wild species (rodents, squirrels and others) is particularly important. The proposed combination ensures a higher immunogenicity percents in immune-castration of pigs, goats, etc, to avoid the unpleasant odor produced in the meat and fat of those animals. Another use of this combination is to control the fertility and aggressiveness of animals of economic importance as bulls, buffaloes, horses and others. Concerning human medicine, the use of this invention has direct application in the treatment of prostate and breast cancers, as well as in uterus, ovary, testicles, sub-maxillary glands cancers, in hypophyseal pathologies and in other hormone-sensitive neoplasia.

Immunogenic preparation of the type of carboxyl terminal as one of the components of the combination.

One of the components of the vaccine, the carboxyl terminal variant, may be in one of the cases constituted by the natural GnRH molecule or one of its mimetics, for example, GnRHm1 with the sequence QHWSYPLRPG (SEQ ID NO: 1) bound to a T helper epitope (830-844) of tetanus toxoid (QYIKANSKFIGITEL) (SEQ ID NO: 2), or to other carriers as the diphtheria toxoid, P64K protein of *Neisseria meningitides*, hepatitis B core antigen, etc, obtained as fusion proteins using an expression system for genetic constructions.

The chemical synthesis, and adjuvation with an oily adjuvant (of the Montanide type) of the complete peptide QHWSYPLRPG QYIKANSKFIGITEL (SEQ ID NO: 4) has shown to have a testosterone ablation potent effect with only 2 immunizations of prepuberous animals and with 3 or 4 immunizations in adult animals. The achieved antibody titers using this variant were of 1/1000-1/2000 for most of the individuals after the fourth immunization reaching 90% of seroconversion.

Amino Terminal; the Second Component of the Combination.

Similarly, the construction of a natural GnRH molecule or one of its mimetics as is the case of the above described GnRHm1 bound by its amino terminal extreme to 830-844 epitope of tetanus toxoid to form the molecule (QYIKANSKFIGITELGGQ HWSYPLRPG) (SEQ ID NO: 6), or the bound of it to its amino-terminal to P48 peptide of P64K protein of *Neisseria meningitides* (IPGVAYTSPE-VAWVGGGGQHWSYPLRP) (SEQ ID NO: 7), or to other carrier molecules of the above mentioned types, constitutes an active component with a higher immunogenic potential against endogenous GnRH as compared to that produced by carboxyl terminal variant already mentioned. Significantly, we have found that individuals immunized with TT-GnRHm1 show natural GnRH seroconversion just after the first immunization reaching antibody titers from 1:6000 to 1:12000 after the third or fourth immunization. In turn, the amino-terminal variant (P48-P64K-GnRHm1) elicits a 90% antibodies response after just one immunization and titers of 1:5000 and 1:12000 after the fourth immunization. Taking into account that the GnRH is a very small autologous molecule conserved in all mammals, the said titers can be considered very significant. This amino terminal variant does not produce, however, a significant superior effect on target organs (prostate, testicles in males or ovaries in female) as compared to carboxyl terminal variant.

FIGURES DESCRIPTION

FIG. 1: Schematic amino-acidic sequence representation of natural GnRH, GnRHm1-TT, TT-GnRHm1, GnRHm1-P48-P64K and P48-P64K-GnRHm1 variants.

FIG. 2: Average anti-GnRH (natural) seroconversion of immunized animals with different GnRH variants bound to TT carrier molecule.

Figure 3:
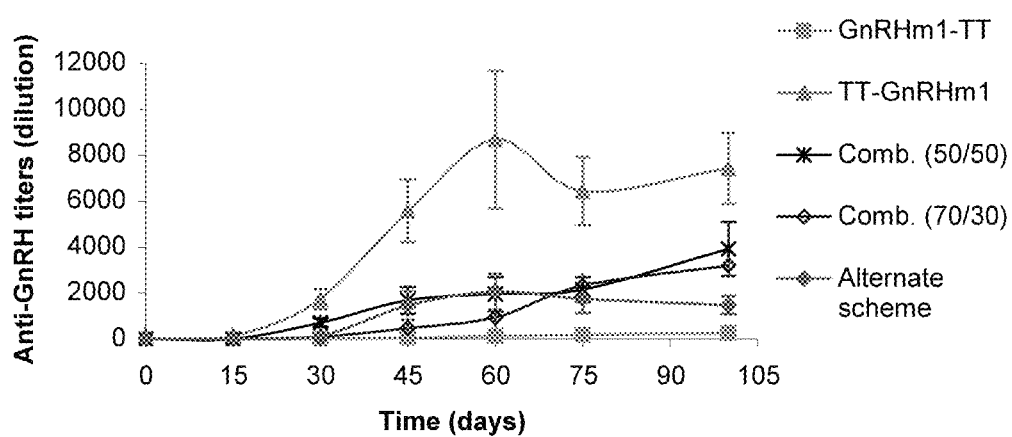

FIG. 3: Anti-GnRH antibodies titers in healthy Copenhagen rats immunized with different variants of GnRH bond to TT carrier molecule.

Figure 4:
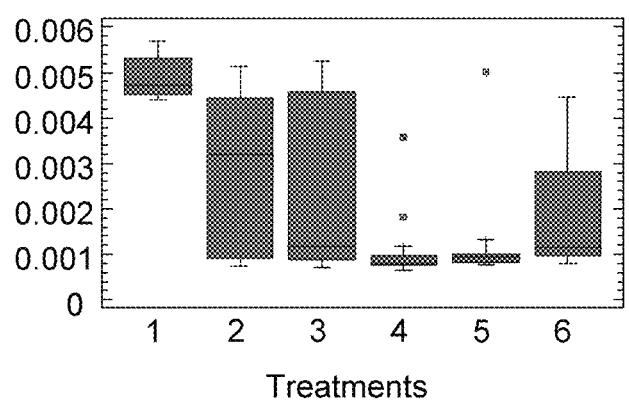

FIG. 4: Testicles weight evaluation at slaughter (100 days). LSD Stat-Graphic statistic evaluation. 1—Placebo, 2—GnRHm1-TT, 3—TT-GnRHm1, 4—Combination 2+3 (50/50), 5—Combination 2+3 (70/30), 6—Alternate scheme.

Figure 5:
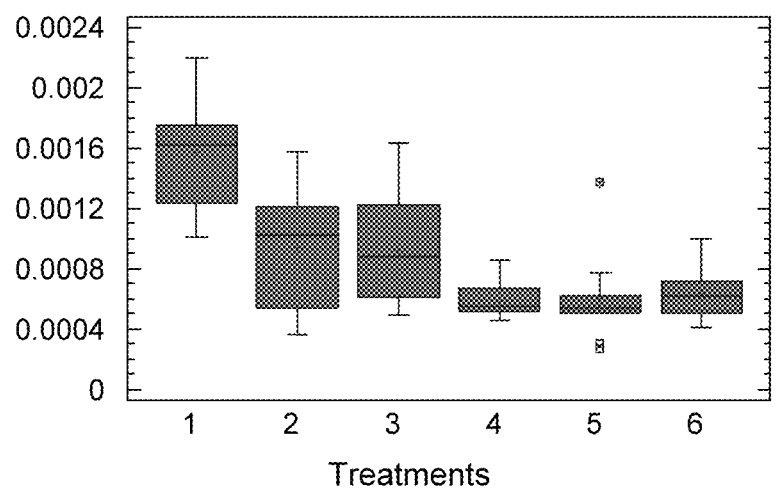

FIG. 5: Prostate weight evaluation at slaughter (100 days). LSD statistical evaluation Stat-Graphic. 1—Placebo, 2—GnRHm1-TT, 3—TT-GnRHm1, 4-Combination 2+3 (50/50), 5—Combination 2+3 (70/30), 6—Alternate scheme.

Figure 6:
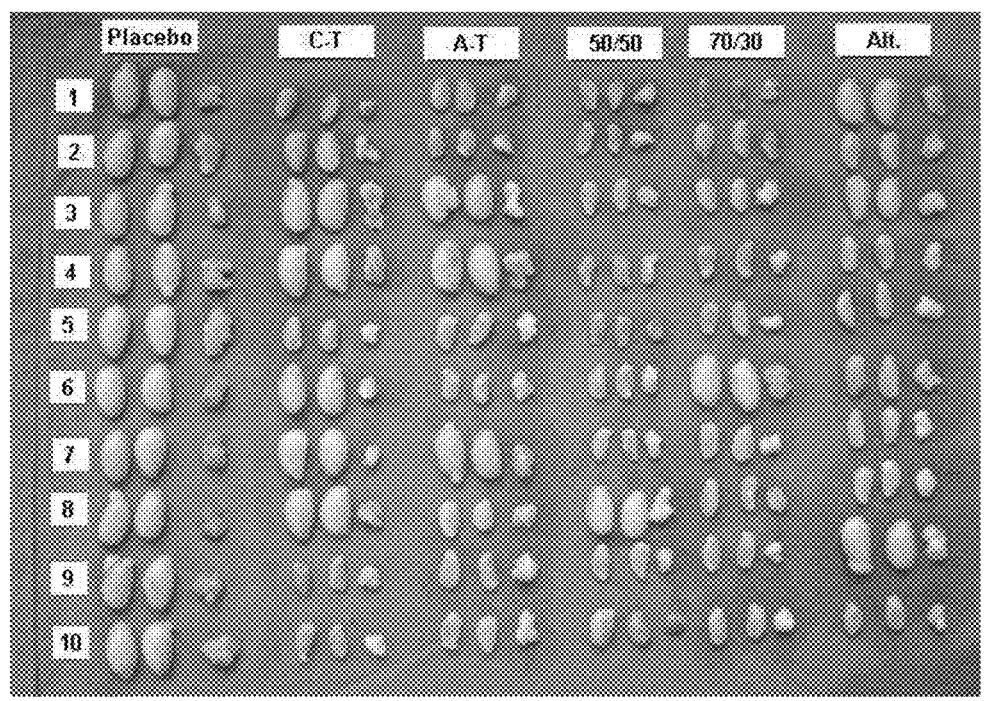

FIG. 6: Macroscopic aspect of the testicles and prostate of all the evaluated animals (n=10 for each group). The groups from left to right are: first—Placebo, second—GnRHm1-TT (C-T), third—TT-GnRHm1 (A-T), fourth—Combination [C-T]+[A-T] (50/50), 5th—Combination [C-T]+[A-T] (70/30) and 6th—Alternate scheme (Alt).

Figure 7:
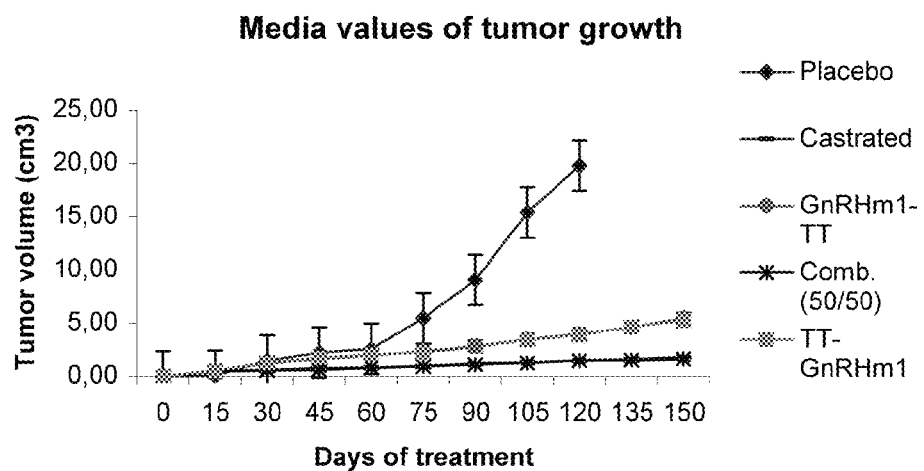

FIG. 7: Media values of tumor volume of different GnRH variants bound to tetanus toxoid carrier molecule.

Figure 8:
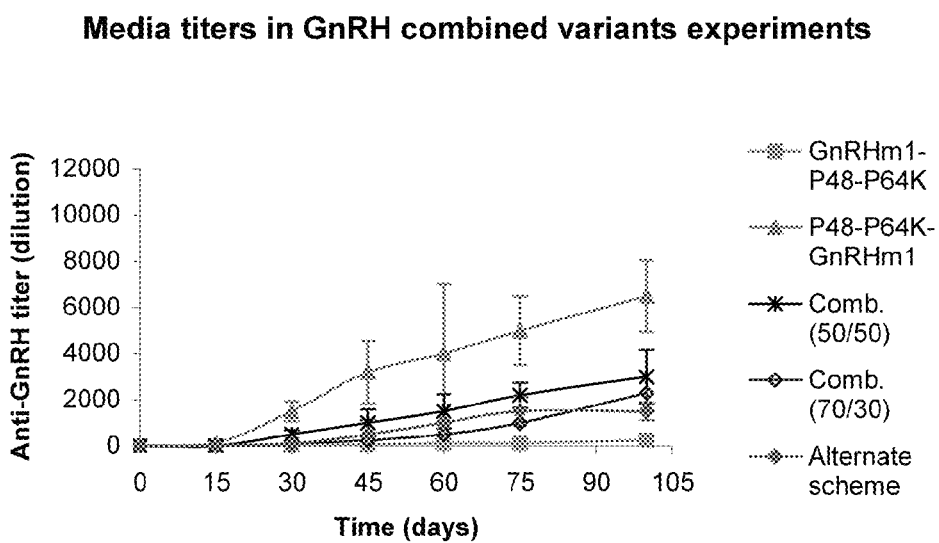

FIG. 8: Anti-GnRH antibodies titers of immunized Copenhagen rats with different GnRH variants bound to a TP48-P64K carrier molecule.

Figure 9:
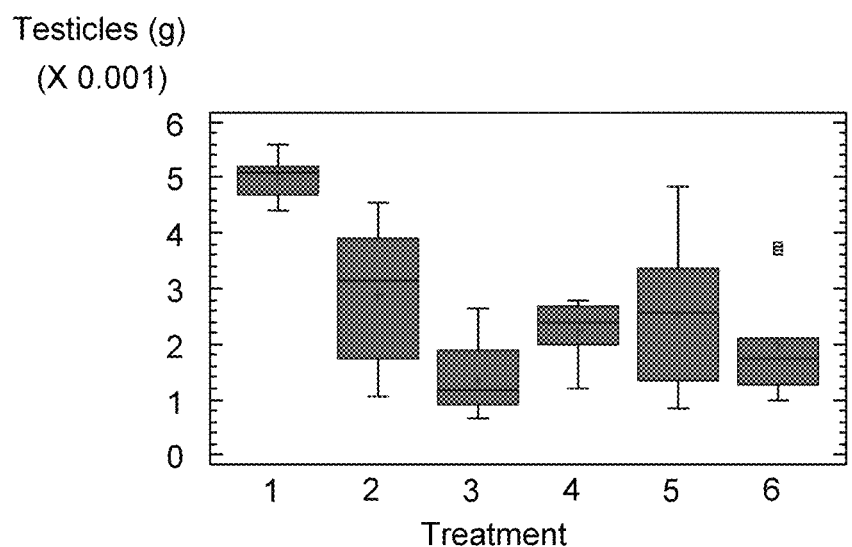

FIG. 9: Testicles weight evaluation at slaughter (100 days). LSD statistical evaluation Stat-Graphic. 1—Placebo, 2—GnRHm1-P48-P64K, 3—P48-P64K-GnTHm1, 4—Combination 2+3 (50/50), 5—Combination 2+3 (70/30), 6—Alternate scheme.

Figure 10:
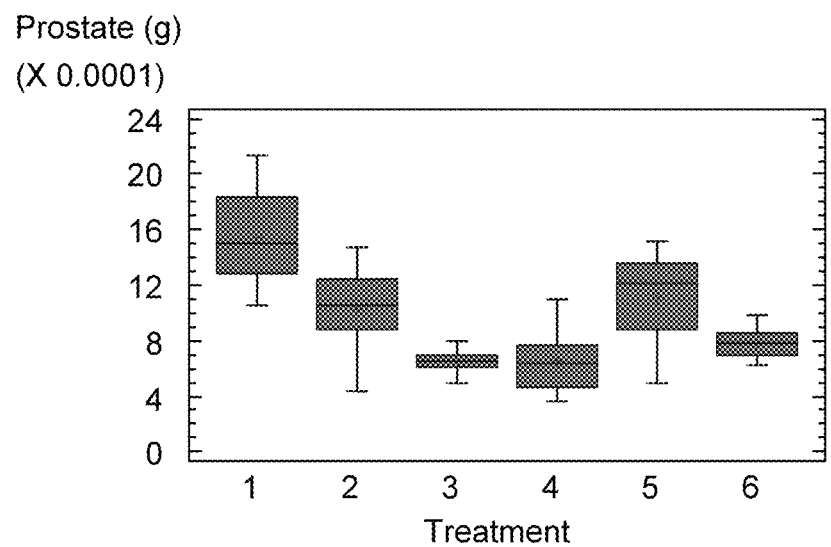

FIG. 10. Prostate weight evaluation at slaughter (100 days). LSD statistical evaluation Stat-Graphic. 1—Placebo, 2—GnRHm1-P48-P64K, 3—P48-P64K-GnTHm1, 4—Combination 2+3 (50/50), 5—Combination 2+3 (70/30), 6—Alternate scheme.

Figure 11:
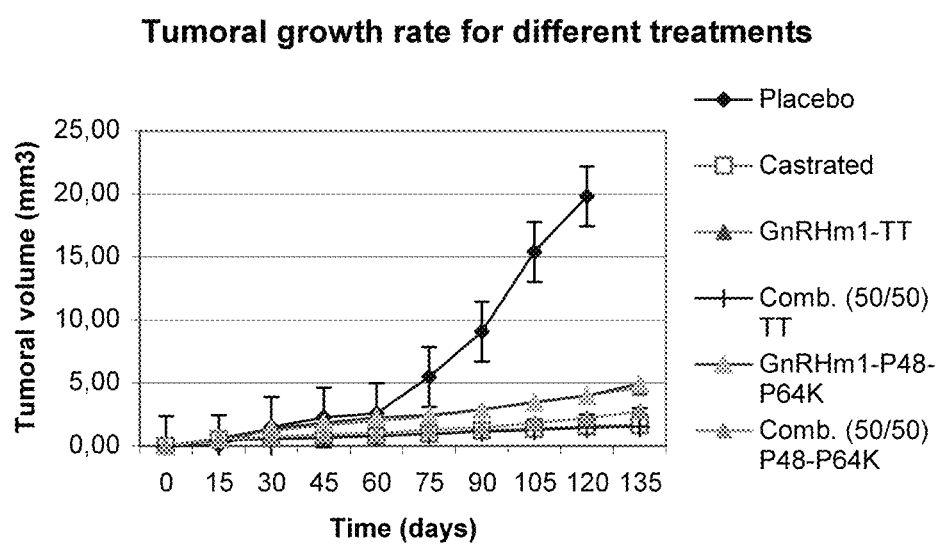

FIG. 11. Tumor growth rate evaluation of the Dunning R3327-H tumor cell line implanted in Copenhagen rats prior to animal immunization.

EXAMPLES

Immunogenicity Experiment and Effect on Target Organs with the GnRH Carboxyl and Amino Terminal Variants Bound to Different Carrier Molecules

Example 1

Immunogenicity of GnRHm1-TT carboxyl- and Amino-Terminal Variants using TT as Carrier Molecule The GnRH amino and carboxyl terminal variants and TT synthesized peptides sequences used in biological assays are described in FIGS. 1a and 1b.

1.1. Experimental Groups
1—Placebo.
2—Carboxyl terminal (GnRHm1-TT) 750 µg of total peptide.
3—Amino terminal (TT-GnRHm1) 750 µg of total peptide.
4—50/50 combination (w/w) in the same emulsion of the carboxyl terminal (GnRHm1-TT)+.amino terminal (TT-GnRHm1) variants; 750 µg of total peptide (375 µg of each one).
5—70/30 (w/w) in the same emulsion of the carboxyl terminal (GnRHm1-TT)+amino terminal (TT-GnRHm1) variants; 750 µg of total peptide (525 µg of GnRHm1-TT and 225 µg of TT-GnRHm1),
6—Alternate immunization with Carboxyl terminal (GnRHm1-TT) 750 µg of total peptide at the 0, 30 and 60 days; and Amino terminal (TT-GnRHm1) 750 µg of total peptide at 15 and 45 days.

In all cases 5 subcutaneous immunizations for each variant were done using Montanide adjuvant.

1.2. Experiment Development:
1.2.1. Immunogenic Preparations, Animals' Immunization and Analysis of Results.
1.2.2. Adjuvation:
The carboxyl terminal peptide variant GnRHm1-TT and/or amino terminal peptide variant TT-GnRHm1 in corresponding doses were resuspended individually in water for injection. Later, a mixture of 50% (v/v) of resuspended peptides and the oily adjuvant was obtained. Finally, the mixture was shacked in e mechanical device for 20 min. to form a milky white emulsion ready to use.
1.2.3. Immunization:
Disposable syringes were loaded with 1 mL of emulsion and subcutaneously injected in dorsal region of 9-12 weeks old Copenhagen rats using a fortnightly scheme.
1.2.4. Measuring the Anti-GnRH Antibodies Titers:
The circulating anti-GnRH antibodies elicited after vaccination were measured using an ELISA (Enzyme—Linked—immunoassay) system. 96 well polystyrene plates were coated with 100 µL of native GnRH peptide (5 µg/ml) in 100 mM $Na_2CO_3$ (pH 9.6) and incubated over night at 4° C. After some washes with PBS 1× (pH 7.4), the plates where blocked with 2% BSA in PBS and incubated for 1 h at 37° C. The animal serum samples were diluted (rates 1/60-1/2000) in PBS containing 1% of BSA, Tween 20 (0.01%, w/v) incubated for 3 h at 37° C. The plates were washed with PBS several times and were put to react with anti-IgG antibodies from rat, conjugated with horseradish peroxidase (SIGMA Biochemical USA). After other washes the plates were incubated with a mixture containing Ortophenilen-diamine (OPD) and $H_2O_2$ substrate in citrate buffer. The titers were expressed as the maximum dilution of samples that reaches values 2 times higher than the assay cutoff value.

1.2.5. Testosterone Levels Determination:

The testosterone levels were determined using TESTO CT2 Kit (CisBio, International, France). 25 μL of each serum sample were added directly in pre-coated tubes. Samples were incubated in duplicate. Finally the tubes were washed with distilled water and read using a gamma. The results were expressed in nmol/L.

1.2.6. Animals' Slaughter and Statistics Analysis:

The animals were anesthetized and slaughtered one month after the $5^{th}$ immunization (100 days) according to good laboratory practices. The significant statistic differences regarding the testicles and prostate size were evaluated using the Duncan test (Stat-Graphic software). Likewise, testosterone levels were analyzed using the same statistic procedure (SAS Institute Inc., SAS/STAT™ User's Guide, Release 6.03 Edition. Cary, N C: SAS Institute Inc., 1988. 1028 pp).

1.3 Experimental Results.
1.3.1 Seroconversion Analysis:

GnRH molecule, as stated before, has a 100% homology in all mammalians and in a high number of superior vertebrates. It also has a very small size (only ten amino-acids), which confers to it a very low immunogenic power in contrast to its high tolerogenic capacity due to its endogenous nature.

In the example we are describing, the group immunized with the amino terminal variant (TT-GnRHm1), achieved a 100% of serocenversion after the first immunization whereas the group immunized with the carboxyl terminal variant (GnRHm1-TT), showed a 90% of seroconversion only after the third immunization. The combination (50/50) with the mixed amino and carboxyl terminal variants had a 100% of seroconversion after the second immunization and finally, the combination (70/30) of the mixture amino and carboxyl terminal variants reached 100% of seroconversion after the third immunization (FIG. 2).

1.3.2. Anti-GnRH Antibodies Titers Evaluation:

The anti-GnRH antibodies titers in serum samples of each experimental group are shown In FIG. 3. As can be seen in the graphic, the group TT-GnRHm1 showed the higher speed of immune response correlated with the emergence of anti-GnRH titers, which ranged between 1/6000 and 1/12000 after 75 and 100 days of the beginning of experiment respectively. The 50/50 and 70/30 combined variants showed similar anti-GnRH antibodies titers but the first one showed greater speed of titers response. The alternate immunization scheme with the GnRHm1-TT and TT-GnRHm1 variants, could not maintain titers as height as the 50/50 combination; however it reaches similar speed in eliciting titers. In the group immunized with the GnRHm1-TT variant, the titers appeared later than in the rest of experimental groups (after the third immunization) and could not reach higher titers levels than 1/1000.

1.3.3. Correlation Between Anti-GnRH Antibodies Titers Elicited Against Different GnRH Regions and the Effect on Target Organs.

The correlation analysis between the anti-GnRH antibodies titers and the effect on target organs (prostate, testicles) was made. As it is shown in FIG. 3, while the immunization with the amino-terminal region TT-GnRHm1 show a height immunogenic profile, the carboxyl terminal variant (GnRHm1-TT) shoed slower seroconvertion and significantly lower antibodies titers against GnRH. At slaughter similar results in the effect on target organs were found. Height titers as 1:12000 were reached by immunized group with amino terminal variant (TT-GnRHm1) producing similar effect on target organs (prostate and testicles) as compared to the group immunized with carboxyl terminal variant (GnRHm1-TT) (FIGS. 4 and 5).

The mixture of different proportions of amino and carboxyl terminal variants in the same immunization scheme, elicits a significantly higher immunological response than that obtained with the individual carboxyl terminal peptide, which produces a significant higher biological effect than the two variants individually administered. Although, it does not reach the absolute titer values as those obtained with the use of amino terminal variant. Similar results were obtained when both peptides were inoculated in an alternate form in the same immunization scheme (FIG. 4, 5, 6).

Example 2

Immunogenicity of GnRHm1-TT Carboxyl- and Amino-Terminal Variants Using P48-P64K as Carrier Molecule

2.1. Experimental Groups:

1—Placebo.

2—Carboxyl terminal (GnRHm1-P48-P64K) 750 μg of total peptide.

3—Amino terminal (P48-P64K -GnRHm1) 750 μg of total peptide.

4—50/50 combination (w/w) in the same emulsion of the carboxyl terminal (GnRHm1-P48-P64K)+.amino terminal (P48-P64K-GnRHm1) variants; 750 μg of total peptide (375 μg of each one).

5—70/30 (w/w) in the same emulsion of the carboxyl terminal (GnRHm1-P48-P64K)+amino terminal (P48-P64K-GnRHm1) variants; 750 μg of total peptide (525 μg of GnRHm1-P48-P64K and 225 μg of P48-P64K-GnRHm1), 6—Alternate (2 and 3) immunization with Carboxyl terminal (GnRHm1-P48-P64K) 750 μg of total peptide at the 0, 30 and 60 days; and Amino terminal (P48-P64K-GnRHm1) 750 μg of total peptide at 15 and 45 days.

In all cases 5 subcutaneous immunizations for each variant were done using Montanide adjuvant.

2.2. Experiment Development:

Immunogenic preparations, animals' immunization and analysis of results and statistical data were processed as described from 1.2.1 to 1.3.3.

2.3. Experimental Results
2.3.1. Seroconversion Analysis:

In this experiment, the group immunized with the amino terminal peptide variant (P48-P64K-GnRHm1) achieved a 100% of seroconversion after the first immunization, while the group immunized with the carboxyl terminal peptide variant (GnRHm1-P48-P64K) show a 70-80% of seroconversion only after the third immunization. However, the carboxyl and amino terminal mixed variants, combination (50/50), exhibited a 100% seroconversion after the second immunization. On the other hand, the carboxyl and amino terminal variant, combination (70/30), and the alternate immunization schemes showed a 100% of seroconversion after the third immunization (FIG. 7).

2.3.2. Anti-GnRH Antibodies Titers Evaluation:

FIG. 8 shows the serum anti-GnRH antibodies titers of each experimental group. In this graphic, it was observed that group P48-P64K-GnRHm1 showed a faster anti-GnRH titers appearance, which ranged between 1/5000 and 1/8000 at the end of the experiment. Within the combined variants, the 50/50 and 70/30 variants elicited similar anti-GnRH antibodies titers. However with the 50/50 variant, the titers showed a faster response. On the other hand, the alternate immunization scheme with the GnRHm1-P48-P64K and P48-P64K-GnRHm1 variants developed similar immunogenic levels to those elicited with 70/30 variant. Though, the titers were not kept as high as for the first one. As to the immunized group with the GnRHm1-P48-P64K variant, the titers appeared later than in the rest of experimental groups, and did not reach levels greater than 1/1000 in the best cases.

2.3.3. Correlation Between Anti-GnRH Antibodies Titers Elicited Against Different GnRH Regions and the Effect on Target Organs.

As it is shown in FIGS. 7 and 8, while the immunization with the P48-P64K-GnRHm1 amino terminal variant elicited a high immunogenicity, the carboxyl terminal variant (GnRHm1-P48-P64K) showed a slower seroconversion and also significantly lower anti-GnRH antibodies titres. The observed differences in seroconversion were not as evident in relation to the target organs effect at slaughter. Thus, titres as high as 1:8000 in immunized group with the amino terminal variant (P48-P64K-GnRHm1) produced similar effects over the target organs (testicles, prostate) than the immunized group with carboxyl terminal variant GnRHm1-P48-P64K) (FIG. 9 y 10)

The carboxyl and amino terminal variants mixed in different proportions in the same immunization scheme, achieves a significantly superior immunological response than the obtained with the individual carboxyl terminal peptide and though lower than the obtained titres with the use of amino terminal variant, the biological effect is significantly superior to the 2 individually administered variants. Similar results were observed when both peptides were inoculated in the same immunization scheme in alternate form (FIGS. 8, 9 and 10).

Example 3

Correlation Between the Humoral Response Elicited Against Different GnRH Regions and the Effect on Target Organs. The Combined Effect Once the antibodies titers were analyzed, a correlation analysis was performed between these titers and the effect on target organs (prostate and testicles). As it is shown in FIGS. 3 and 8, it was observed a completely different behavior regarding their immunogenic capacity in experimental groups 2 and 3, corresponding to the carboxyl and amino terminal variants. Thus, while the amino terminal, represented by TT-GnRHm1 and P48-P64K-GnRHm1TT peptides, showed a faster anti-GnRH antibodies production in the used models, as well as high titers against this hormone, much slower seroconversion and significantly lower antibodies titers against GnRH were achieved with carboxyl terminal variants (GnRHm1-TT and GnRHm1-P48-P64K). These seroconversion and serum titers determination, despite being different, produced similar results in their action on the target organs at animals slaughter time evaluation. Thus it could be observed that antibody titers as high as 1:12000 in the groups immunized with the amino terminal variant, exerted similar effects on the target organs (prostate and testicles) than the groups immunized with carboxyl terminal variant (FIGS. 4 & 5, and 9 & 10). However, if the carboxyl and amino terminal variants are mixed in different proportions in the same immunization scheme, a significantly higher immunological response than that of the individual carboxyl terminal peptide is obtained. This response does not reach titers values as high as those with the amino terminal variant, but it produces a biological effect significantly higher than the 2 individually administered variants. Similar results were obtained when both peptides were inoculated in the same immunization scheme in alternate form (FIGS. 4, 5, 9 and 10).

These results lead to the conclusion that the free carboxyl group in GnRH strongly stimulates the immunological response against this hormone when it is bound to a carrier molecule by the amino terminal extreme, or by other amino-acid away from carboxyl. On the contrary, the GnRHm1-TT which when it is bound to a carrier molecule by its carboxyl terminal extreme, seems to be compromising the exposition of this region to the immunological system and solely exposing the amino extreme. This amino terminal region does not have the same high immune-stimulating capacity as the first one, but it is able to generate a response that although it is 10 times weaker, it similarly neutralizes the hormone when it is administered in doses equal to the TT-GnRHm1 variant.

Based on these findings, we can affirm that in the case of GnRH the most immunogenic regions are not necessarily the immune-neutralizing zones. The same occurs with other proteins and peptides.

The above mentioned results permit us to conclude that the simultaneous use in a mixture of 2 GnRH variants or its mimetics bound to a carrier molecule, in one case by its amino terminal and in the other by its carboxyl terminal in the same immunization scheme, produces a synergism of the anti-GnRH immunological response. In this case, the effect on the immunological response is higher than just the summatory of the expected effects in the uncombined variants.

The markedly synergistic effect on the reduction of the prostate and testicles size was observed with the 50/50 and 70/30 variant combinations, when the mixture of peptides was used for the immunization process. The alternate and sequential schemes produce also a combined effect, but it is weaker than the simultaneous one. This effect was mainly materialized in the atrophy of testicles and prostate.

As treatment effect ($E_{treatment}$) was considered the unity, minus the mean weight ratio of target organs (prostate and testicles) in the treated animals ($P_{treatment}$), and target organs mean weight in placebo animals ($P_{placebo}$):

$$E_{treatment}=1-(P_{treatment}/P_{placebo}) \tag{1}$$

As shown in tables 1a and 1b, the experimental effect achieved for 50/50 combination of carboxyl and amino terminals on the prostate and testicles was higher than the expected theoretical effect, thus proving the synergic effect of this combination in reducing the target organs size using any of the described molecules in FIG. 1. In the case of the two peptide 70/30 combinations results very much similar to those of the carboxyl+amino terminal (50/50) combination. With the alternate immunization scheme, regarding the biological effect on target organs (prostate and testicles), only the sumatory of the effects was observed, although the achieved titers were superior to individual immunization variants.

The overall synergistic effect achieved by the combined immunization as compare to the individual variants for each of the peptides when they were used by separate wile immunizing healthy adult animals is shown in Tables 1a and 1b.

TABLE 1

Summary of theoretical and experimental values regarding the effect on testicles and prostate using carboxyl and amino terminal variants of GnRHm1 with two different carrier molecules.
A) GnRHm1-TT y TT-GnRHm1 molecules effect,
B) GnRHm1-P48-P64K y P48-P64K-GnRHm1 molecules effect.

| Treatments | Effect on Testicles | Theoretical effect on Testicles | Effect on Prostate | Theoretical effect on Prostate |
|---|---|---|---|---|
| A) | | | | |
| Placebo | 0.00 | — | 0.00 | — |
| Carboxyl terminal (GnRHm1-TT) | 0.43 | — | 0.41 | — |
| Carboxyl + Amino terminal (GnRHm1-TT + TTGnRHm1) (50/50) | 0.80 | 0.74 | 0.75 | 0.65 |
| Carboxyl + Amino terminal (GnRHm1-TT + TTGnRHm1) (70/30) | 0.77 | 0.74 | 0.70 | 0.65 |
| Amino terminal (TT-GnRHm1) | 0.55 | — | 0.42 | — |
| Carboxyl + Amino terminal (GnRHm1-TT + TTGnRHm1) Alternate Immunization | 0.68 | — | 0.60 | — |
| B) | | | | |
| Carboxyl terminal (GnRHm1-P48-P64K) | 0.42 | — | 0.34 | — |
| Carboxyl + Amino terminal (GnRHm1-P48-P64K + P48-P64K-GnRHm1) (50/50) | 0.73 | 0.70 | 0.58 | 0.53 |
| Carboxyl + Amino terminal (GnRHm1-P48-P64k + P48-P64K-GnRHm1) (70/30) | 0.72 | 0.70 | 0.55 | 0.53 |
| Amino terminal (P48-P64K-GnRHm1) | 0.49 | — | 0.28 | — |
| Carboxyl + Amino terminal (GnRHm1-P48-P64K + P48-P64K-GnRHm1) Alternate Immunization | 0.60 | — | 0.49 | — |

Example 4

Therapy Experiments Using the Individual GnRHm1-TT and TT-GnRHm1 Variants and their Combinations (GnRHm1-TT+TT-GnRHm1) in Adult Copenhagen Rats Implanted with Dunning R3327-H Cell Line 4.1. Animals, Tumoral Model:
Tumor fragments of (2×2×2 mm) of murine tumoral model Dunning R3327-H were subcutaneously (s.c) transplanted in a distal zone of the right posterior extremity of adult Copenhagen rats with a weight of 150 to 200 g. (CENPALAB, Cuba). This is a hormone-dependent highly differentiated tumoral cell line with a volume doubling time of 17 days. To determine the tumor growth rate, the tumors were routinarially measured once a week. The tumoral volume was calculated using the formula $4/3\, \pi\, r^3$ where r is the radious mean. The animals were maintained with commercial diet and fresh water at libitum.

4.2. Experimental Design:
Experimental Groups:
1. Placebo animals (immunized with PBS in Montanide ISA 51).
2. Surgically castrated animals.
3. GnRHm1-TT peptide immunized animals.
4. Animals immunized with a mixture (50/50) of peptides GnRHm1-TT+TT-GnRHm1.
5. GnRHm1-P48-P64K peptide immunized group.
6. Animals immunized with a mixture (50/50) of peptides GnRHm1-P48-P64K+P48-P64K-GnRHm1.

4.3. Animals Treatments:
The animal treatment was carried out using a therapeutic model, inoculated with fragments of Dunning R3327-H tumor cell line as it is described in paragraph 3.1.1. The therapeutic interventions (immunizations) started when the tumors reached approximately 10 mm of diameter. Immunizations were carried out fortnightly.
Doses used in the experiment for groups from 3 to 7, were the same as those described in paragraph 1.1.

4.4. Experimental Results:
Tumor growth rate evaluation in Copenhagen rats implanted with Dunning R3327-H tumor cell line.
As shown in FIG. 11, while in the placebo group an abrupt growth of the tumor was observed, in the castrated and immunized groups a marked inhibition of tumor growth was achieved. Out of all variants, the castrated animals and GnRHm1-TT+TT-GnRHm1 (50/50) and GnRHm1-P48-P64K+P48-P64K-GnRHm1 (50/50) combined variants showed the greatest inhibitory capacity. The inhibition was very similar for these three experimental variants and turned to be significantly different compared to placebo and other groups.

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Mar. 19, 2015. The sequence listing.txt file is 3 kb in size.

The invention claimed is:

1. A method to treat prostate cancer comprising administering to a mammal in need thereof a pharmaceutical composition comprising a mixture of two GnRH variants, wherein one of the variants contains a carrier molecule bound at the carboxyl terminus of the GnRH variant and the other variant contains the same or another carrier molecule bound at the amino terminus of the GnRH variant, said variants selected from the group consisting of SEQ ID NOS: 4-7, wherein the carboxyl terminal variant is 50%-70% of the mixture, and the amino terminal variant is 30%-50% of the mixture.

2. The method of claim 1 wherein the mixture of GnRH amino and carboxyl terminal variants are obtained through chemical binding, by synthesis, conjugation, or cloning.

3. The method of claim 1, wherein the GnRH variants are chemically synthesized using D amino-acids.

4. The method of claim 1, wherein the binding to a carrier molecule is carried out either by chemical conjugation or directly synthesized in the same process with a carrier molecule.

* * * * *

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial sequence
<220> FEATURE:
<223> OTHER INFORMATION: Mimetics of natural GnRH

<400> SEQUENCE: 1

Gln His Trp Ser Tyr Pro Leu Arg Pro Gly
1               5                   10

<210> SEQ ID NO 2
```

-continued

```
<211> LENGTH: 15
<212> TYPE: PRT
<213> ORGANISM: Artificial sequence
<220> FEATURE:
<223> OTHER INFORMATION: T helper epitope of the tetanus toxoid 830-844.

<400> SEQUENCE: 2

Gln Tyr Ile Lys Ala Asn Ser Lys Phe Ile Gly Ile Thr Glu Leu
1               5                   10                  15

<210> SEQ ID NO 3
<211> LENGTH: 15
<212> TYPE: PRT
<213> ORGANISM: Neisseria meningitidis
<220> FEATURE:
<223> OTHER INFORMATION: peptide P48-P64K of Neisseria meningitides

<400> SEQUENCE: 3

Ile Pro Gly Val Ala Tyr Thr Ser Pro Glu Val Ala Trp Val Gly
1               5                   10                  15

<210> SEQ ID NO 4
<211> LENGTH: 27
<212> TYPE: PRT
<213> ORGANISM: Artificial sequence
<220> FEATURE:
<223> OTHER INFORMATION: Chemical synthesis of the peptide.GnRHm1Tox.

<400> SEQUENCE: 4

Gln His Trp Ser Tyr Pro Leu Arg Pro Gly Gly Gly Gln Tyr Ile Lys
1               5                   10                  15

Ala Asn Ser Lys Phe Ile Gly Ile Thr Glu Leu
            20                  25

<210> SEQ ID NO 5
<211> LENGTH: 27
<212> TYPE: PRT
<213> ORGANISM: Artificial sequence
<220> FEATURE:
<223> OTHER INFORMATION: Chemical synthesis of the peptide GnRHm1P48.

<400> SEQUENCE: 5

Gln His Trp Ser Tyr Pro Leu Arg Pro Gly Gly Gly Ile Pro Gly Val
1               5                   10                  15

Ala Tyr Thr Ser Pro Glu Val Ala Trp Val Gly
            20                  25

<210> SEQ ID NO 6
<211> LENGTH: 27
<212> TYPE: PRT
<213> ORGANISM: Artificial sequence
<220> FEATURE:
<223> OTHER INFORMATION: GnRHm1 bonded at its amino-terminal end to
      epitope 830-844 of the tetanus toxoid

<400> SEQUENCE: 6

Gln Tyr Ile Lys Ala Asn Ser Lys Phe Ile Gly Ile Thr Glu Leu Gly
1               5                   10                  15

Gly Gln His Trp Ser Tyr Pro Leu Arg Pro Gly
            20                  25

<210> SEQ ID NO 7
<211> LENGTH: 27
<212> TYPE: PRT
<213> ORGANISM: Artificial sequence
<220> FEATURE:
```

```
<223> OTHER INFORMATION: GnRHm1 bonded at its amino-terminal end to the
      peptide P48 of the protein P64K of Neisseria meningitidis

<400> SEQUENCE: 7

Ile Pro Gly Val Ala Tyr Thr Ser Pro Glu Val Ala Trp Val Gly Gly
1               5                   10                  15

Gly Gly Gln His Trp Ser Tyr Pro Leu Arg Pro
            20                  25

<210> SEQ ID NO 8
<211> LENGTH: 10
<212> TYPE: PRT
<213> ORGANISM: Artificial sequence
<220> FEATURE:
<223> OTHER INFORMATION: Synthethic sequence

<400> SEQUENCE: 8

Gln His Trp Ser Tyr Gly Leu Arg Pro Gly
1               5                   10
```